(12) United States Patent
Miller et al.

(10) Patent No.: US 7,681,466 B2
(45) Date of Patent: Mar. 23, 2010

(54) PROGRAMMABLE RANDOM ACCESS SAMPLE HANDLER FOR USE WITHIN AND AUTOMATED LABORATORY SYSTEM

(75) Inventors: Kerry Lynn Miller, Elkton, MD (US); Peter Louis Gebrian, Wilmington, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 475 days.

(21) Appl. No.: 11/742,897

(22) Filed: May 1, 2007

(65) Prior Publication Data
US 2008/0271546 A1    Nov. 6, 2008

(51) Int. Cl.
*G01N 1/00* (2006.01)
(52) U.S. Cl. .................................................. 73/864.31
(58) Field of Classification Search .................. None
See application file for complete search history.

(56) References Cited

U.S. PATENT DOCUMENTS

| | | | |
|---|---|---|---|
| 4,861,553 A | | 8/1989 | Mawhirt et al. |
| 5,008,082 A | | 4/1991 | Shaw |
| 5,350,564 A | * | 9/1994 | Mazza et al. .................. 422/63 |
| 5,972,295 A | | 10/1999 | Hanawa et al. |
| 6,290,907 B1 | | 9/2001 | Takahashi et al. |
| 6,358,472 B1 | | 3/2002 | DeYoung et al. |
| 6,843,357 B2 | * | 1/2005 | Bybee et al. ............. 198/345.3 |
| 6,890,485 B1 | | 5/2005 | Stylli et al. |
| 7,011,792 B2 | | 3/2006 | Mimura et al. |
| 2006/0148063 A1 | | 7/2006 | Fauzzi et al. |

\* cited by examiner

*Primary Examiner*—Robert R Raevis
(74) *Attorney, Agent, or Firm*—Leland K. Jordan

(57) ABSTRACT

A method and a device for removing high priority samples from a primary conveyor and transferring such samples directly to an analyzer's sampling location even if other samples have been previously removed from the conveyor and are in a queue to be analyzed.

11 Claims, 21 Drawing Sheets

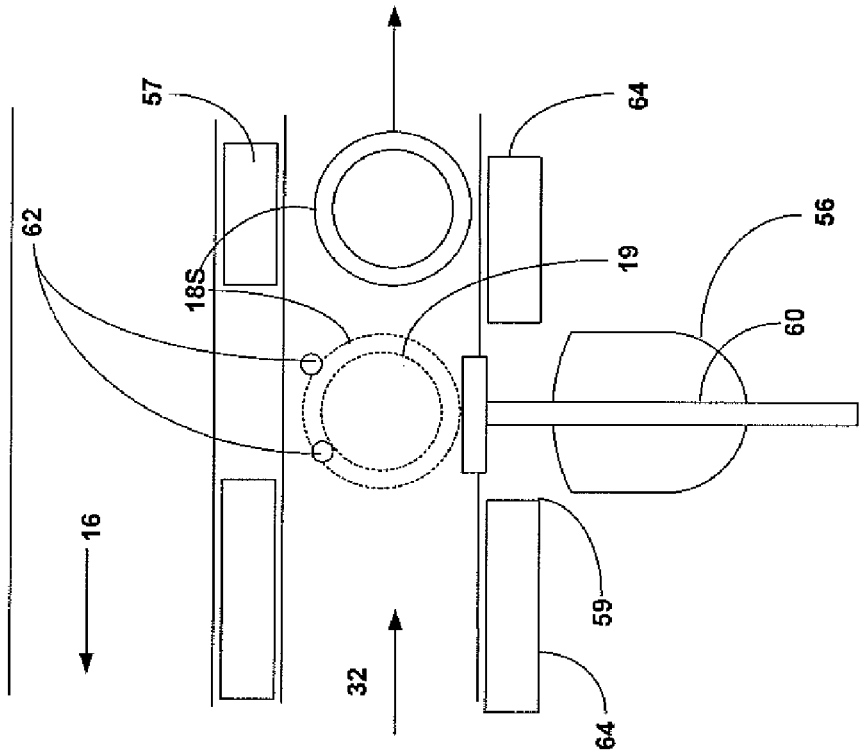
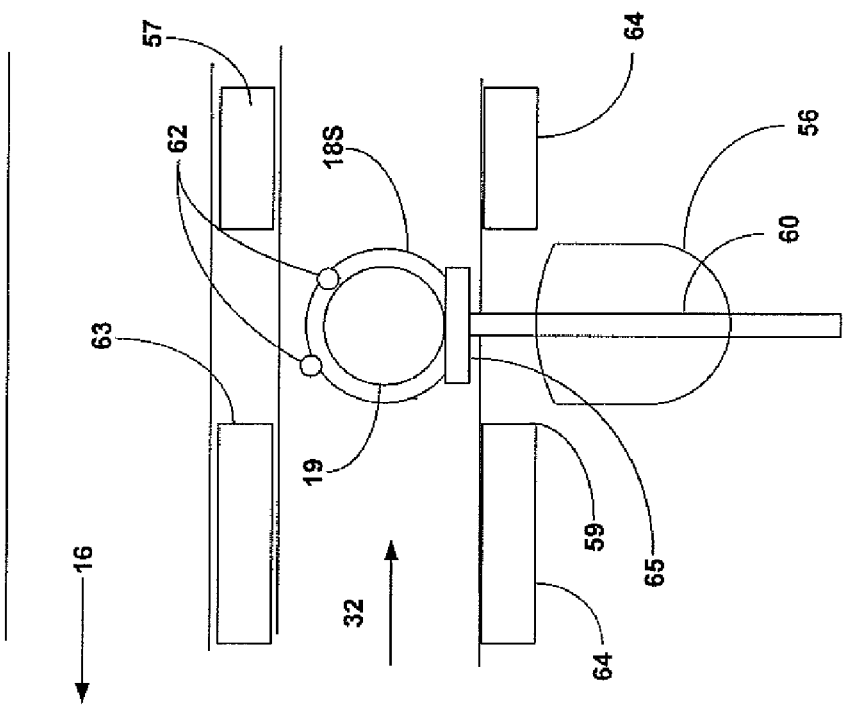
FIG. 15A
FIG. 15B

US 7,681,466 B2

PROGRAMMABLE RANDOM ACCESS SAMPLE HANDLER FOR USE WITHIN AND AUTOMATED LABORATORY SYSTEM

FIELD OF THE INVENTION

The present invention relates to an automated clinical sample treatment and transportation system with one or more independent processing stations having samples supplied for testing thereto by a conveyor. More particularly, the present invention relates to a sample handling device for enabling samples to be presented to a processing station from the conveyor in a prioritized, independent order without delays from other samples scheduled to be processed by the same processing station.

BACKGROUND OF THE INVENTION

Clinical diagnostic analyzers are being developed with increasing levels of complexity and sophistication in order to fully automate the performance of chemical assays and immunoassays of biological fluid samples such as urine, blood serum, plasma, cerebrospinal liquids and the like, these fluid samples almost universally being contained in open or capped sample tubes. Generally, chemical reactions between an analyte in a patient's biological sample and reagents used during performing the assay result in generating various signals that can be measured by the analyzer. From these signals the concentration of the analyte in the sample may be calculated.

A wide variety of automated chemical analyzers are known in the art and are continually being improved to increase analytical menu and throughput, to reduce turnaround time, and to decrease requisite sample volumes. See for example, U.S. Pat. Nos. 6,103,193, and 6,027,691 and 5,482,861. Such improvements, while necessary in themselves, may be hampered if sufficient corresponding advances are not made in the automation of pre-analytical sample preparation and handling operations like sorting, batch preparation, centrifugation of sample tubes to separate sample constituents, cap removal to facilitate fluid access, and the like.

Automated clinical sample treatment and transportation systems generally include conveyor systems for conveying specimens to processing stations, such as those described in U.S. Pat. Nos. 6,060,022, and 5,972,295. Typical of such systems, a sample is transported to an analyzer by a primary conveyor and shuttled onto an analyzer-specific buffer lane that transports samples to the sampling area of an adjacent analyzer in the order in which they were placed. A problem with such systems arises when an incoming sample has a higher priority for testing than samples already on the primary conveyor or already in the processing station-specific buffer lane. One solution is to control the conveyor so that all samples preceding the higher priority are forced to by-pass the target processing station and/or to move the samples already in the specific buffer lane back onto the primary conveyor in order to allow the higher-priority sample to be processed without further delay. Both of these solutions are undesirable since the overall throughput of the sample handling treatment and transportation system is reduced when samples are inefficiently passed more than once around the primary conveyor.

U.S. Pat. No. 7,011,792 discloses an automatic analyzing apparatus having a plurality of analyzer units for serum, blood plasma and urine arranged along a main transfer line for transferring a sample rack from a rack providing portion to an analyzer specific sampling lane to a rack storage area. Each newly added sample follows a previously added sample on the main transfer line and/or within the analyzer specific sampling lanes. In the event of a high-priority sample, samples are forwarded directly to the analyzer unit at which the operation priority is assigned, however it is not clear how one sample on the main transfer line can by-pass another.

U.S. Pat. No. 6,290,907 discloses a sample handling system with a transportation line for transporting a sample rack, a rack loading device for loading the transportation line, a rack storage device for storing the sample rack transported by the transportation line, a plurality of treating units for treating samples held in a sample rack. The transportation line includes pairs of plural partitive line units and treating units. In the case of high-priority samples, an operator sets such samples at an emergency sample mounting position and are provided with priority over normal sample racks in a normal sample mounting areas. Again, the high-priority samples are not given priority over samples already on the transportation line nor over sample racks buffered in the sample processing area of an analyzer.

U.S. Pat. No. 6,060,022, automatically presents pre-treated samples in open containers to robotic devices operated in conjunction with independent stand-alone analyzers. No special provision is made for high-priority samples.

U.S. Pat. No. 5,972,295 discloses an automatic analyzing apparatus having a rack supply unit and a transfer line for transferring a sample rack supplied from the rack supply unit to a sampling position within an analyzing unit. An emergency (high-priority) sample input unit is provided so that the high-priority sample rack can be placed at the entrance of the conveying line giving priority over ordinary sample racks in the rack supply unit. However, the high-priority sample rack is not given priority over sample racks already on the conveying line nor over sample racks buffered in the sample processing area of an analyzer.

Although these prior art systems have advanced the art of sample handling and processing, what has not been addressed is the challenge of enabling samples to be presented to a processing station from the conveyor in a prioritized, independent order without delays from other samples scheduled to be processed by the same processing station.

SUMMARY OF THE INVENTION

The present invention provides a method and a device for removing high priority samples from a primary conveyor and transferring such samples directly to an analyzer's sampling location even if other samples have been previously removed from the conveyor. All samples removed from the conveyor are transferred onto a sample storage buffer and the storage buffer is controlled to present the highest priority sample to the analyzer's sampling location. Alternately, the storage buffer can be controlled to present samples to the analyzer's sampling location in the order the samples were removed from the conveyor. In another embodiment, the storage buffer can be controlled to present samples to the analyzer's sampling location in accord with the time required to analyze the sample or in any other preferred order. This new method improves the capability to operate a clinical laboratory's automated sample treatment and transportation system by providing samples removed from a conveyor with "preferred access" to an analyzer's sampling location.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
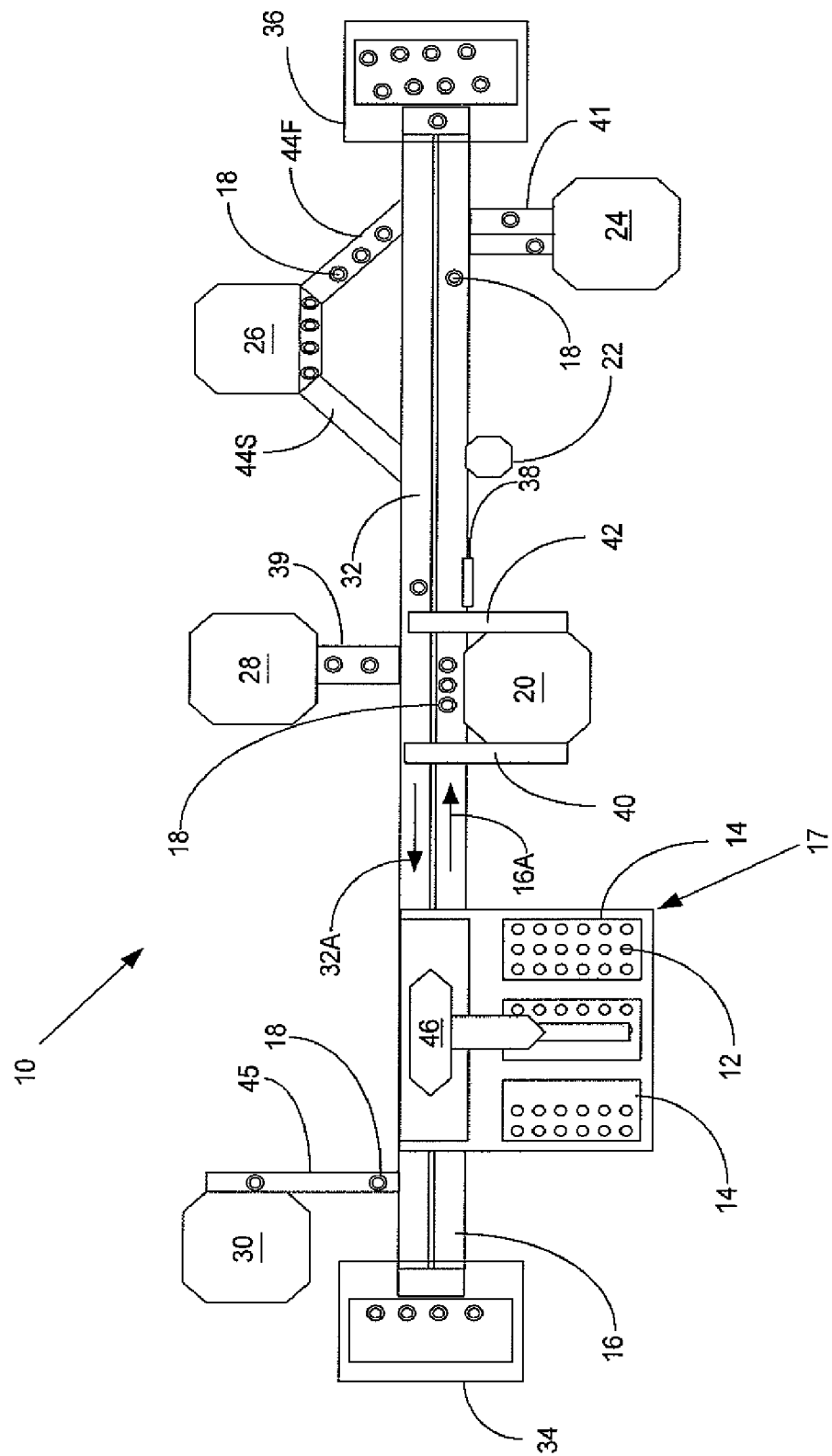
FIG. 1 is a simplified schematic plan view of a prior art automated sample handling system including a conveyor controlled in cooperation with several chemical analysis pre-treatment devices and analyzers in which the present invention may be advantageously employed.

Referring to FIG. 1, there is illustrated an automated clinical chemistry sample handling system 10 capable of automatically pre-processing and handling as necessary multiple sample containers 12, typically test tubes 12 which may be capped or un-capped containing patient samples to be analyzed and presented to system 10 in multiple sample racks 14. Each of the sample containers 12 is provided with container identification indicia, such as a bar code, indicating a patient's identification, as well as, optionally, other procedures to be accomplished upon the sample therein. Sample racks 14 may have additional identification indicia thereon.

Figure 2:
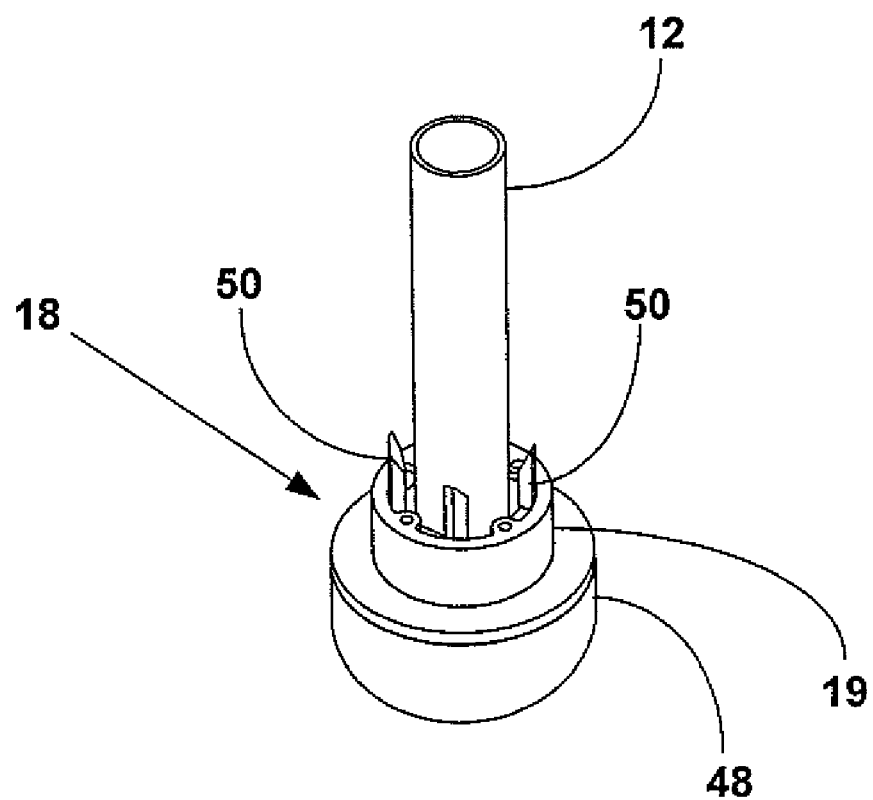
FIG. 2 is a simplified perspective view of a sample tube and sample tube carrier used in the sample handling system of FIG. 1.

Sample handling system 10 comprises an operating base on which a first moving, for example being belt-like or of rollers or links, conveyor track 16 transports a plurality of individual sample tubes 12 carried in sample tube carriers 18 like seen in FIG. 2 in a first direction indicated by arrow 16A from a sample tube loading/unloading station 17 to an automated centrifuge 20 to an automated tube de-capper 22 for automatically removing caps from capped sample tubes 12 and to at least one conventional clinical analyzer 24, 26, 28 and 30 before a second belt-like conveyor track 32 returns each sample tube 12 in a second direction 32A opposed to direction 16A to the sample tube loading/unloading robotic station 17. Sample tube carrier transfer and buffering stations 34 and 36 are provided for transferring sample tube carriers 18 between tracks 16 and 32 as well as for retaining sample tube carriers 18 in a temporary buffer inventory. Sample tube carriers 18 may be buffered in temporary inventory for a number of reasons, including possible re-testing or additional testing, to facilitate testing of high-priority samples, reducing analyzer back-log of samples awaiting analysis and the like. It will be understood that more than four analyzers 24, 26, 28 and 30 may be linked together and be accessible by conveyor tracks 16 and 32. Sample handling system 10 has a number of sensors 38 for detecting the location of a sample tube 12 by means of identifying indicia placed on or within each sample tube carrier 18. Conventional bar-code readers or radio-frequency locating devices may be employed in such tracking operations.

Centrifuge 20 and each analyzer 24, 26, 28 and 30 are generally equipped with appropriate robotic mechanisms 40 and 42 or analyzer tracks 44 for removing a sample tube carrier 18 from conveyor track 16 or 32, moving the sample tube carrier 18 to and from centrifuge 20, to and from or into and out of analyzers 24, 26, 28 and 30 onto track 16 or 32. Typically, the loading/unloading station 17 also includes X-Y-Z robotic arms 46 conventionally equipped with clamping mechanisms to remove sample tubes 12 from racks 14 and to place tubes 12 into tube carriers 18. After all tests to be conducted on a sample in a sample tube 12 are completed, X-Y-Z robotic arms 46 remove sample tubes 12 from tube carriers 18 and replace tubes 12 in racks 14 for removal from system 10.

Sample handling system 10 is controlled by a conventional computer preferably a microprocessor based central processing unit CPU housed as part of or separate from the system 10 to move the sample tube carrier 18 to each operating device 20, 24, 26, 28 and 30 whereat various types of processing occurs. The CPU controls sample handling system 10 according to software, firmware, or hardware commands or circuits like those used on the Dimension® clinical chemistry analyzer sold by Dade Behring Inc. of Deerfield, Ill., and are typical of those skilled in the art of computer-based electromechanical control programming.

FIG. 1 illustrates two different configurations of robotic mechanisms 40 and 42 for removing and replacing a sample tube 12 from conveyor tracks 16 and 32, in particular separate robotic mechanisms 40 and 42 are shown as moving the sample tube 12 into and then out of centrifuge 20, respectively, while only a single robotic mechanism 44 is employed for moving the sample tube carrier 18 into and out of analyzer 28 from track 32. Similarly, analyzer 24 is illustrated as having a pair of analyzer tracks 41 operating in parallel to transfer sample tube carriers 18 into and out of analyzer 24 from track 16. Alternately, analyzer 26 is illustrated as having a pair of first and second analyzer tracks 44F and 44S operating in series to transfer sample tube carrier 18 into and out of analyzer 26 and from track 16 and onto track 32, respectively. Even further, analyzer 30 is illustrated as having a single analyzer track 45 operable to transfer sample tube carrier 18 into and out of analyzer 30 from track 32. Finally, analyzer 28 is illustrated as having a robotic device 39 operable to transfer sample tube carriers 18 into and from analyzer 28 from track 32. All of these configurations are known in prior art systems and all lack the ability to remove a number of sample tube carriers 18 from tracks 16 or 32 and to present the sample tube carriers 18 to an analyzer in a "random" sequence, a random sequence being a sequence other than the sequential sequence at which the sample tube carriers 18 were removed from tracks 16 or 32. Clearly, the ability to simply and easily buffer a number of sample tube carriers 18 and to then present sample tube carriers 18 in a desired order to an analyzer is a desirable improvement in prior methods for assigning priorities for sample testing within an automated sample handling system like system 10.

FIG. 2 is an elevation view of an exemplary sample tube carrier 18 for transporting a sample tube container 12, carrier 18 comprising a generally cylindrical lower carrier body 48 having a central, cylindrical hole depending from a top surface of the carrier body 48, a raised central portion 19 and at least two vertically oriented arms 50 extending a distance upwards above body 48, arms 50 adapted to constrain tube 12 in a generally vertical and concentric orientation.

Figure 3:
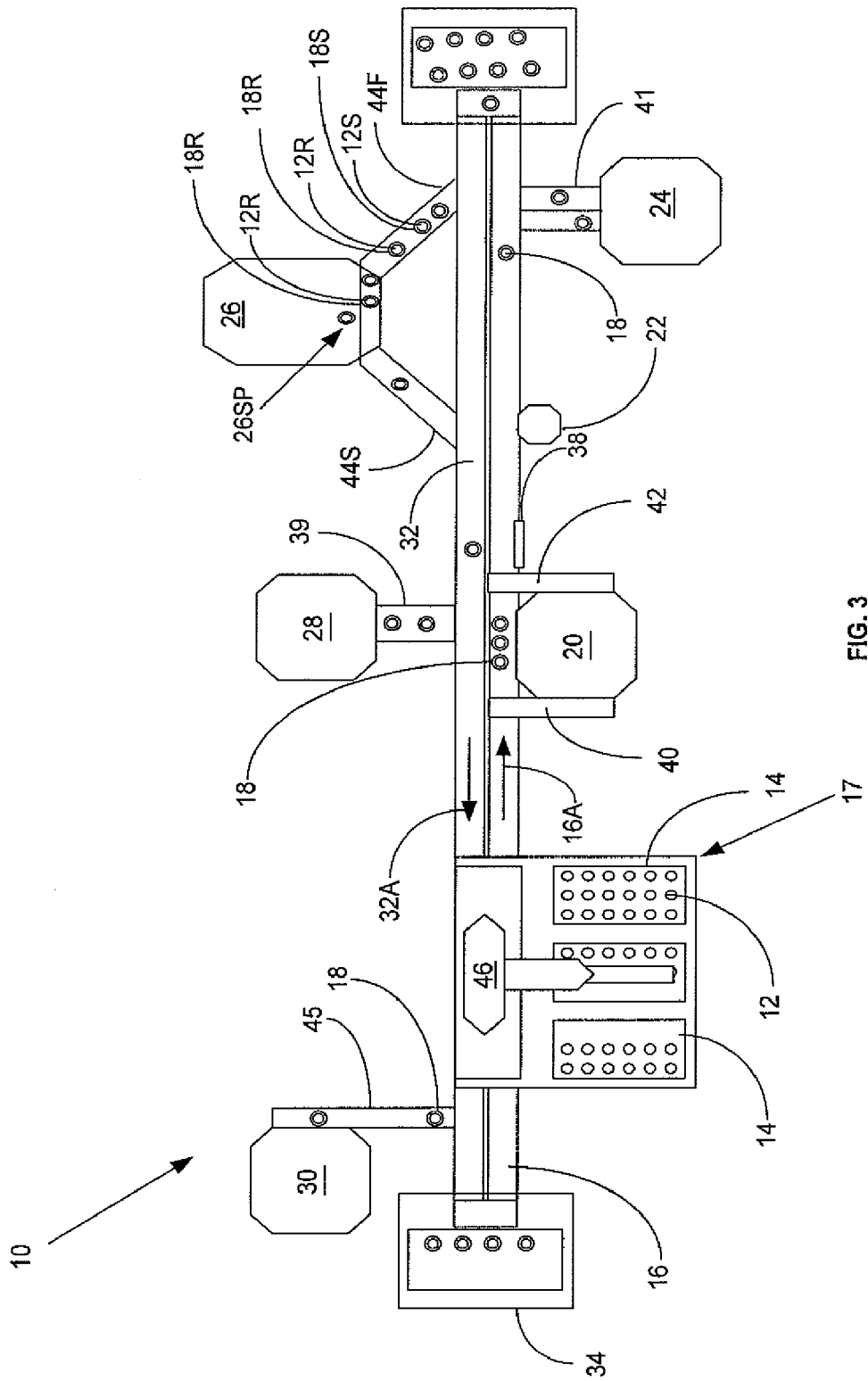
FIG. 3 is a view of the sample handling system of FIG. 1 illustrating a sample handling challenge to be addressed by the present invention.

FIG. 3 illustrates a typical instance addressed as in the prior art by which a special sample tube 12S is to be analyzed by clinical analyzer 26, for example on a high-priority or emergency basis. In prior art systems, even if sample tube 12S is placed on conveyor track 16 by loading/unloading station 17 in a high-priority rack or loading lane and transported directly to analyzer 26, upon arrival of a sample tube carrier 18S at analyzer 26, a number of "routine" sample tubes 12R in sample tube carriers 18 may be found to be buffered in first analyzer track 44F awaiting sampling at a sampling portion or position 26SP associated with analyzer 26. In this event, one option for processing special sample tube 12S is to control track 44F so as to feed all of the "routine" sample tube carriers 18R to second analyzer track 44S and onto track 32 so that access to sampling portion 26SP can be achieved; however, if this option is exercised, all of the released "routine" sample tube carriers 18R must then travel back to analyzer 26 on tracks 32 and 16 before being analyzed, adversely affecting throughout. Another option is for special sample tube carrier 18S to remain on track 32 or in buffer 44F until the "routine" sample tubes 12R have been processed in sampling portion 26SP, and to then process special sample tube 12S in a normal course of time, which option adversely increases the amount of time before special sample tube 12S can be sampled and processed. Neither of these optional solutions is desirable for performance and/or throughput reasons. It should be understood that the above description of performance and/or throughput difficulties experienced in prior art systems is not restricted to a particular analyzer like analyzer 26. Similar difficulties also exist at centrifuge 20 when sample preparation is required, and/or at analyzer 24 having tracks 41 operating in parallel to transfer sample tube carrier 18S into and from analyzer 24. Similarly, difficulties also exist at analyzer 30 having a single analyzer track 45 to transfer sample tube carrier 18S into and from analyzer 30 and at analyzer 28 having robotic device 39 to transfer sample tube carriers 18S into and from track 16 and onto track 32.

Figure 4:
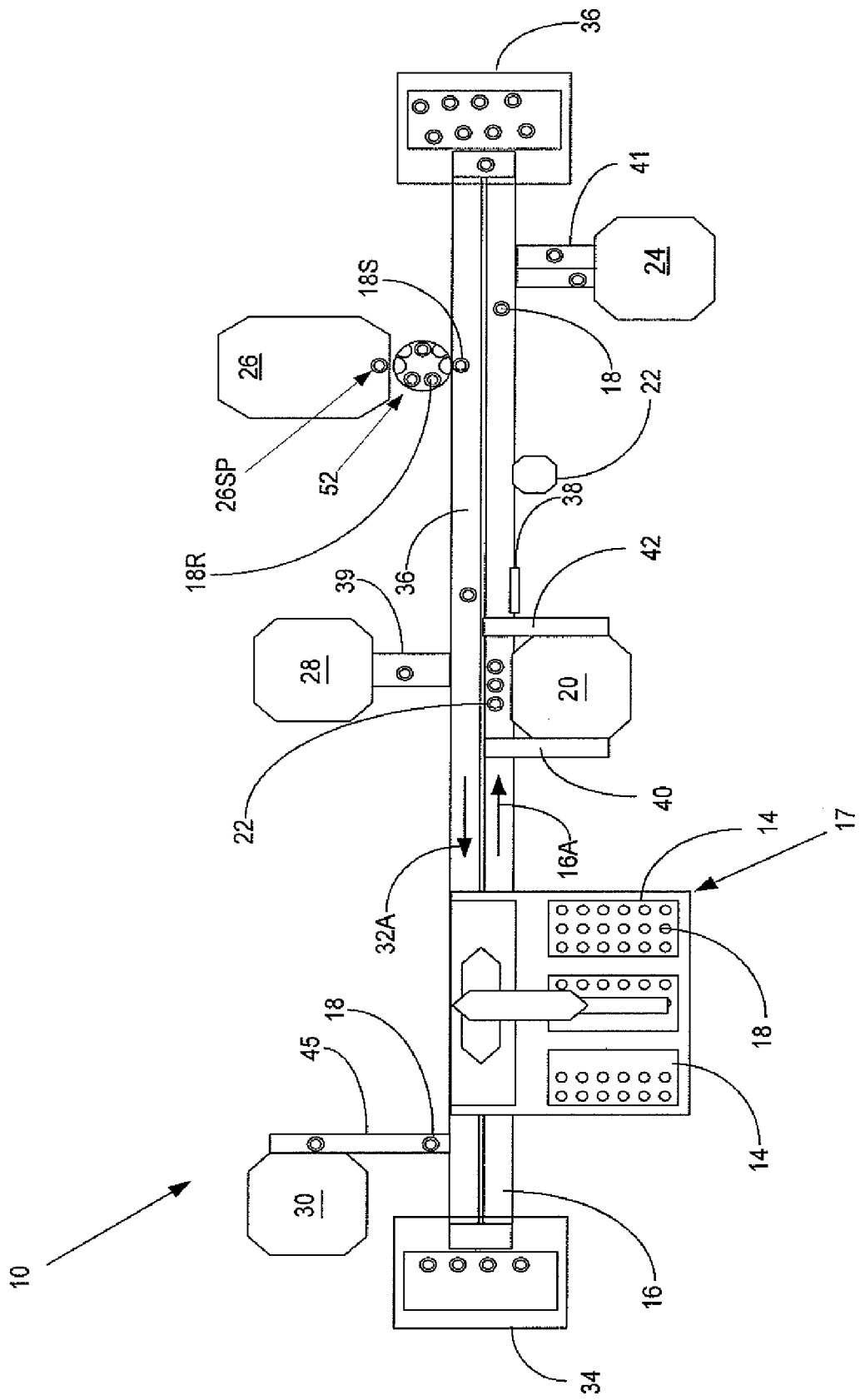
FIG. 4 is a view of the prior art automated sample handling system of FIG. 1 illustrating a sample handling buffer exemplary of the present invention.
Figure 5:
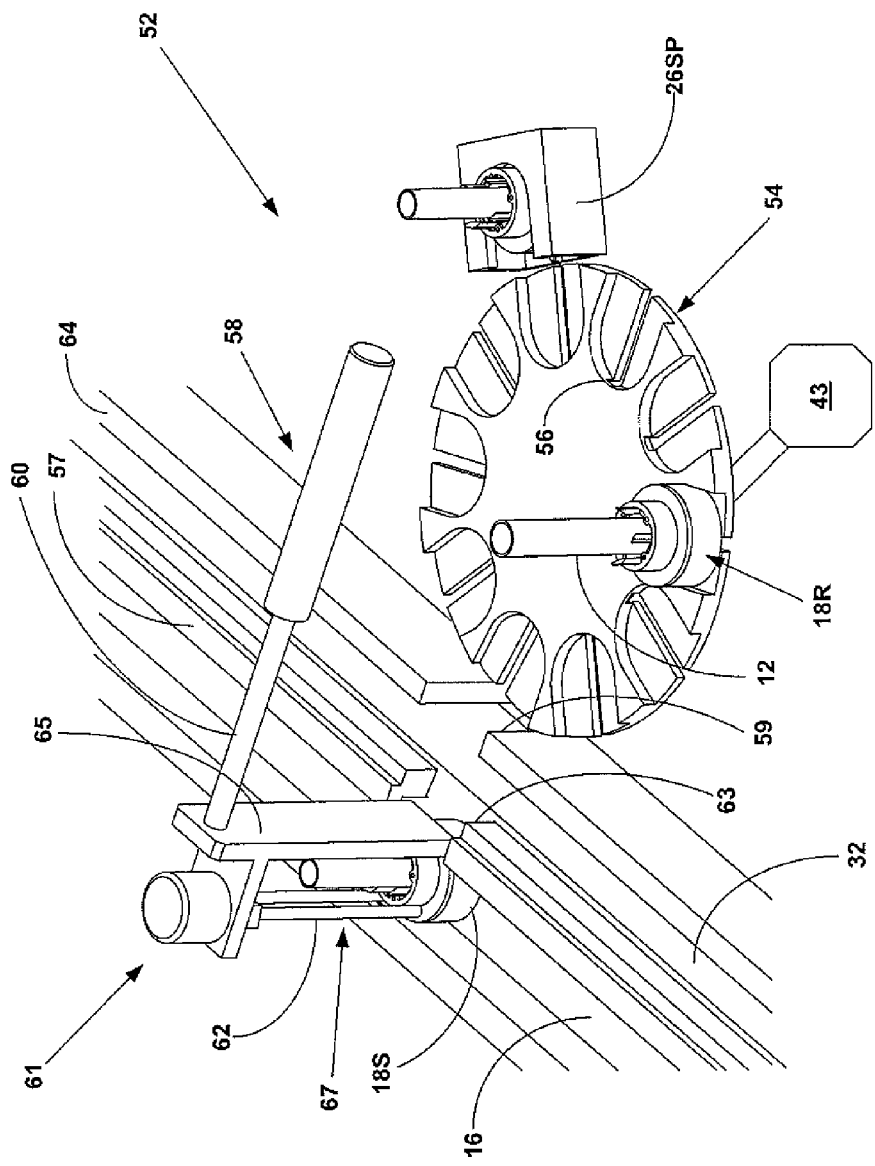
FIG. 5 is a simplified perspective view of the sample handling buffer of FIG. 4 capturing a sample tube carrier conveyed on a track within the automated sample handling system of FIG. 1.

As seen in FIG. 4, the present invention provides a sample handling buffer 52 for enabling a single sample tube carrier 18, for example special sample tube carrier 18S, to be presented to a processing station, analyzer 26 in this example, from conveyor 32 in a random, independent, "out of turn" order without delays from other routine sample tube carriers 18R already scheduled to be processed by the same analyzer 26. It should be appreciated that the processing station may equally well be a pre-analytical sample processing device, such as centrifuge 24. Sample handling buffer 52 is operated so as to remove sample tube carriers 18 from either of tracks 16 or 32 and to present sample tube carriers 18 to a sampling portion or position 26SP associated with analyzer 26, for example, in an order that is independent from the order in which the sample tube carriers 18 were removed from tracks 16 or 32. Sample handling buffer 52 thereby provides a method by which a special sample tube carrier 18S to be analyzed by clinical analyzer 26 on a high-priority or emergency basis can by-pass a number of "routine" sample tube carriers 18R that may have previously been removed from track 32 and are awaiting sampling at sampling position 26SP. As explained below, the present invention thus overcomes the above described disadvantages in performance and/or throughput experienced in prior art systems FIG. 5 illustrates sample handling buffer 52 as comprising an actuator 43 schematically indicated as being adapted to cause a sample carrier holder 54 (in the form of a carousel in the embodiment shown) to place a sample carrier 18 proximate sampling position 26SP. The sample carrier holder carousel 54 having a number of carrier holding zones 56 formed therein. The carrier holding zones 56 are sized to accept a sample tube carrier 18 holding a sample tube 12. In order to provide for presenting sample tube carriers 18 to an analyzer in a "random" sequence, an important feature of carousel 54 is the ability to align carrier holding zones 56 proximate sampling position 26SP in a sequence other than the sequential sequence at which the sample tube carriers 18 are placed into carrier holding zones 56. In the instance that carousel 54 is generally round, this may be accomplished by adapting actuator 43 to bi-directionally rotate carousel 54. In the event that carousel 54 has a different configuration, for example a continuous track-like configuration, actuator 43 would be similarly adapted to bi-directionally drive a track-like carousel. A carrier shuttle 58 disposed above carousel 54 and tracks 16 and 32 comprises a shuttle actuator 60 with carrier escapement device 61 on its distal end, escapement device 61 comprising a pair of carrier shuttle rods 62 and a carrier push plate 65 positioned therefrom to define a carrier capture zone 67, sized appropriately to capture a sample carrier 18 on tracks 16 or 32 therein. Openings 63 are formed in track rails 64 alongside and separating tracks 16 and 32 such that carrier shuttle 58 can moveably slide a sample tube carrier 18 from either of track 16 or 32 into a carrier holding zone 56 by activating shuttle actuator 60 from a fully or partially extended condition to a closed condition as seen in the progression of operating conditions seen in FIGS. 5, 6 and 7.

Figure 6:
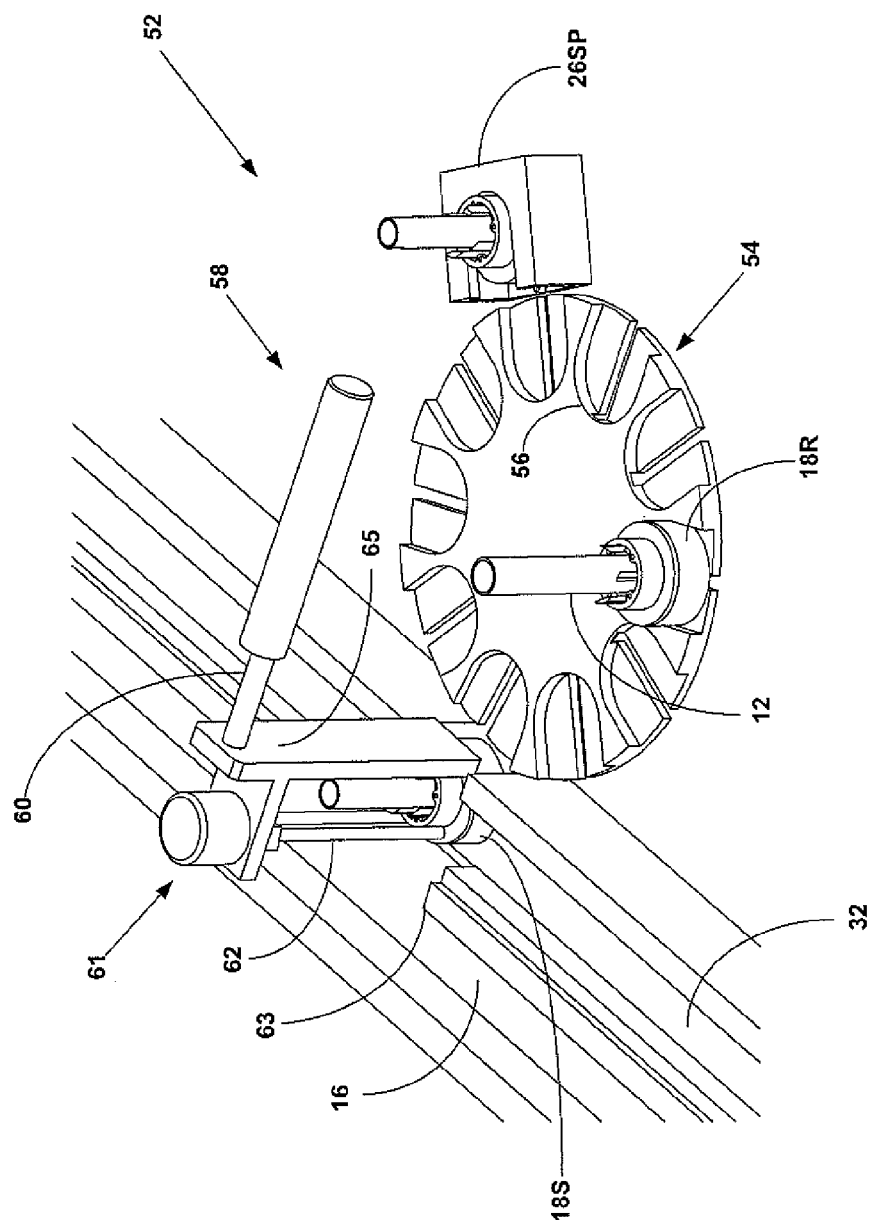
FIG. 6 is a simplified perspective view of the sample handling buffer of the present invention transferring the sample tube carrier illustrated as being captured in FIG. 5 towards a carrier carousel portion of the present invention.

FIG. 5 particularly illustrates a first stage in the sample carrier removal process wherein a special sample carrier 18S on track 16 is captured or engaged by carrier escapement device 61 at a location proximate opening 63 in rail 57. For purposes of illustration, a previously removed routine sample carrier 18R is shown already supported by rotatable carrier carousel 54. FIG. 6 particularly illustrates a further stage in the sample carrier removal process wherein shuttle actuator 60 has been partially retracted to moveably slide sample carrier 18S from track 16, through opening 63 and onto track 32. Next, FIG. 7 particularly illustrates an even further stage in the sample carrier removal process wherein shuttle actuator 60 has been more fully retracted so as to moveably slide sample carrier 18S from track 32, through opening 59 and onto a carrier holding zone 56 in rotatable carrier carousel 54. Finally, FIG. 8 particularly illustrates an even further stage in the sample carrier removal process wherein shuttle actuator 60 has released sample carrier 18S into carrier holding zone 56 in rotatable carrier carousel 54 which is then rotated "counterclockwise" towards sampling position 26SP (For purposes of simplicity, of "routine" sample tube carrier 18R is not shown). As described in conjunction with FIG. 12, carrier escapement device 61 is operable to capture, retain and release a sample carrier 18 as necessary to enable transfer of a selected or special sample carrier 18S from and to either track 16 or 32 and to and from any one of the number of carrier holding zones 56 within rotatable carrier carousel 54.

Figure 9:
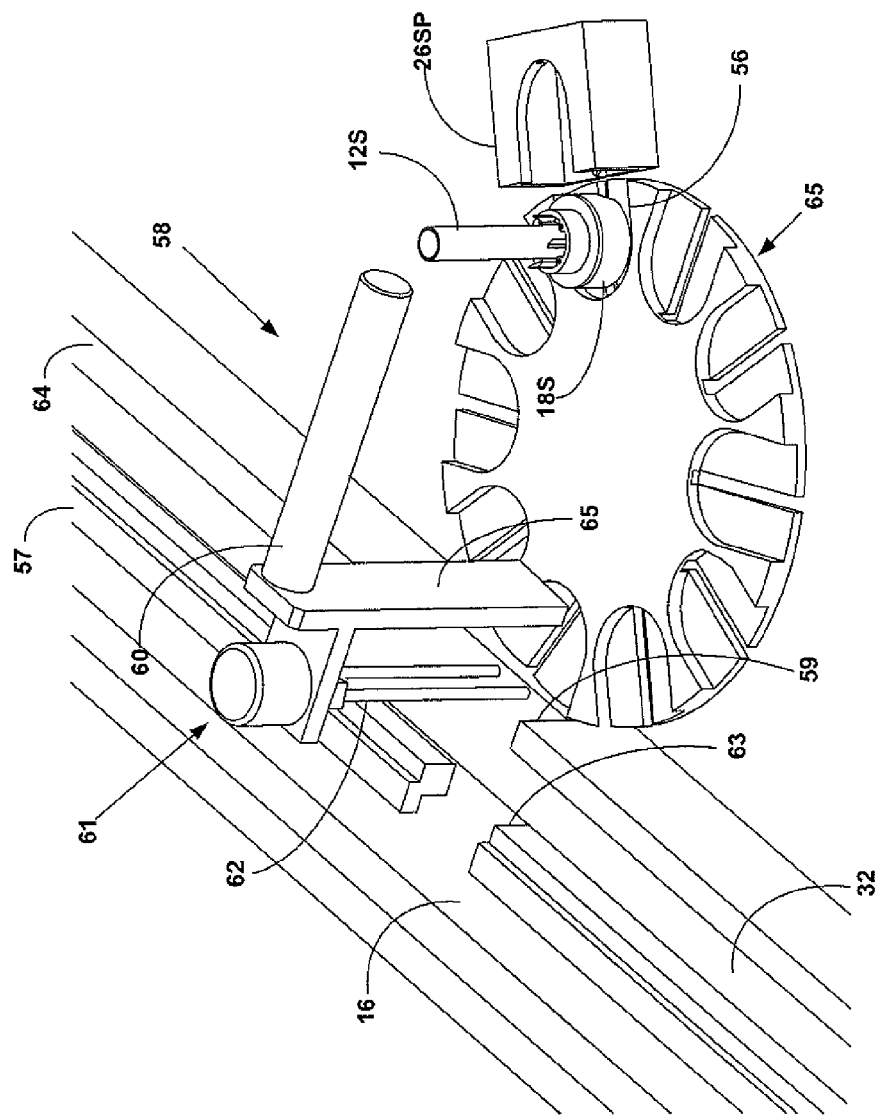
FIG. 9 is a simplified perspective view of the carrier carousel portion of the present invention having placed the sample tube carrier captured in FIG. 5 proximate or at the sampling portion of an analyzer of FIG. 1.

Sample carrier holder carousel 54 is positioned proximate sampling portion 26SP of analyzer 26 as shown in FIG. 9 and advantageously is shaped as a circular plate and is rotatable using a suitable conventional source of rotary motion. Consequently, any carrier holding zone 56 on carousel 54 may be rotated into alignment with sampling portion 26SP and in an aligned orientation, a sample tube carrier 18S holding special sample tube 12S may then be transferred, for example by carrier posts 69 (FIG. 10) described hereinafter from the aligned carrier holding zone 56 into a sampling location in sampling portion 26SP. Alternately, analyzer 26 may be equipped with a moveable sampling probe capable of aspirating liquid from tube 12S without removing tube 12S from carrier holding zone 56 on carousel 54 so that it is not required that sample tube 12S be transferred from the aligned carrier holding zone 56 into sampling portion 26SP. A robotic-assisted moveable sampling probe is but one example of such a system.

As a consequence of carousel 54 being able to support a number of sample tube carriers 18 and to be randomly rotated in either direction so as to expeditiously bring any of the sample tube carriers 18 into sampling portion 26SP of analyzer 26, the sample handling buffer 52 of the present invention provides a device and method for controlling the priority at which sample tubes 12 are made available for testing by an analyzer like analyzer 26. Clearly, carousel 54 may be installed in conjunction with any of the sample processing devices illustrated in FIG. 3 or their equivalents without departing from the scope of the present invention. This is a key feature of the present invention that overcomes many shortcomings of prior art systems wherein samples are tested in the order removed from tracks 16 or 32 or else lower priority sample are removed from a testing location so that higher priority samples may be more quickly analyzed.

After a suitable amount of sample has been withdrawn from sample tube 12 in sample tube carrier 18, carousel 54 may be rotated to re-align the sample tube carrier 18 with openings 59 in track rail 64. Carrier shuttle 58 may be activated to extend shuttle actuator 60 thereby urging carrier push plate 65 and sample tube carrier 18 through openings 59 and 63 in order to replace sample tube carrier 18 on track 16 or 32. In the same manner that carousel 54 is operable for controlling the priority at which sample tubes 12 are made available for testing, carousel 54 is also able to control the priority at which sample tubes 12 may be replaced on track 16 or 32 for testing by a different analyzer. If no additional tests are scheduled to be performed on a given sample tube 12 by any of the analyzers within sample handling system 10, carriers 18 can be placed on track 32 to minimize time "on-board" system 10 in the event that additional tests are to be conducted by analyzers not connected to sample handling system 10 if desired.

Figure 10:
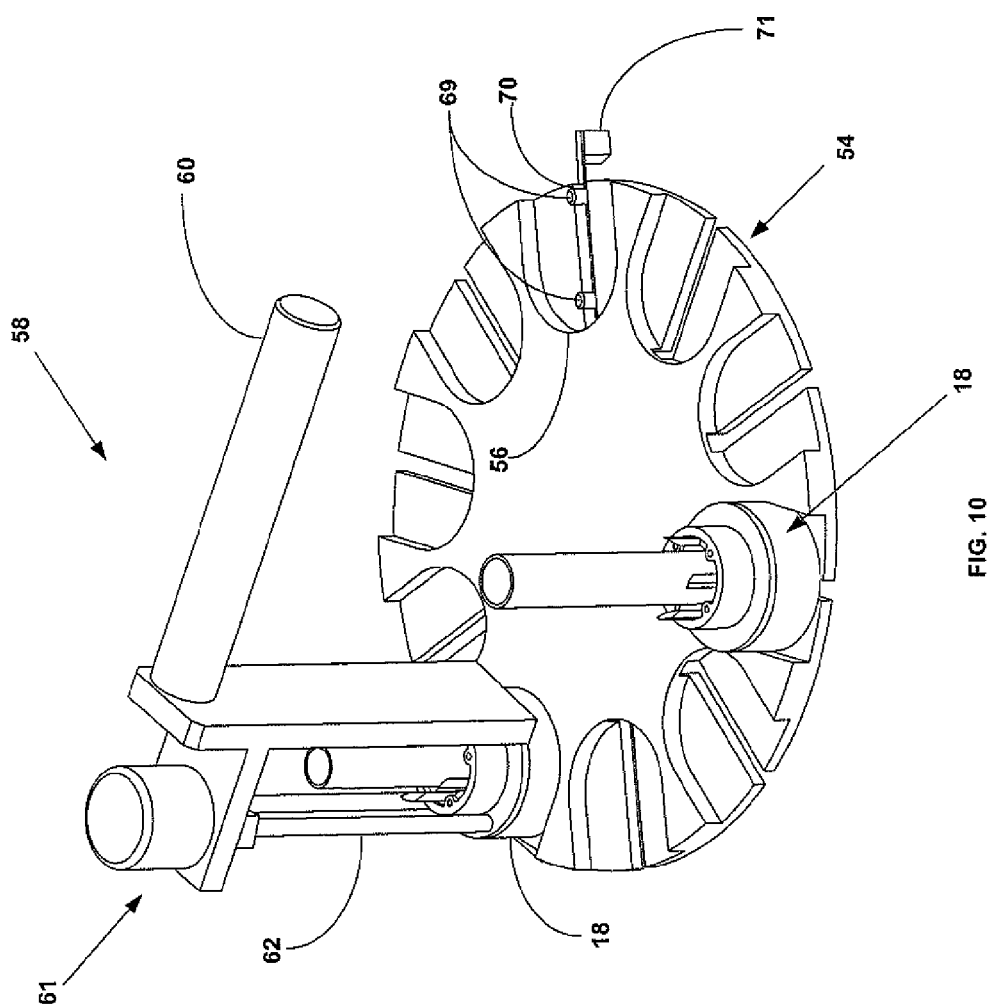
FIG. 10 is a simplified perspective view of a pair of moveable carrier posts in a "capture" position advantageously employed in the present invention.
Figure 10A:
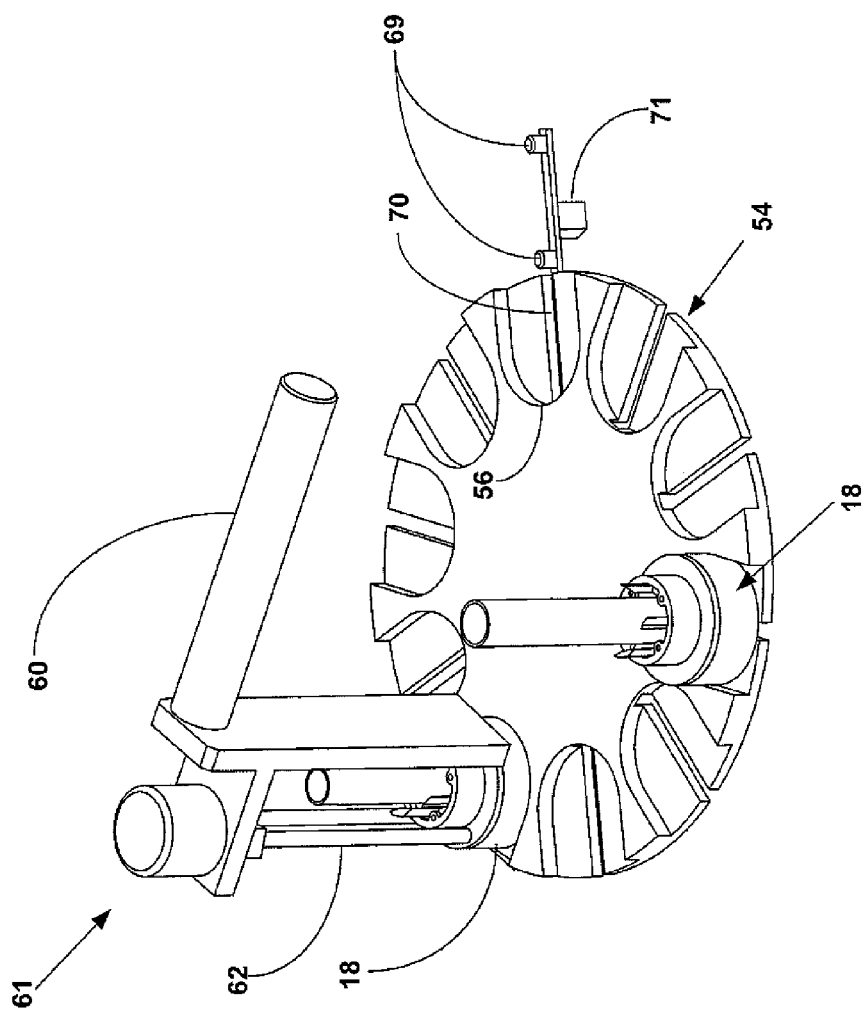
FIG. 10A is a simplified perspective view of the carrier posts of FIG. 10 in a "sampling" position advantageously employed in the present invention.

In an exemplary embodiment like seen in FIG. 10, a pair of carrier pawls 69 spaced apart to hold a sample carrier 18 are linearly translatable within an open carrier holding zone groove 70 formed in the base of carrier holding zone 56 using a conventional source of linear motion 71. The posts 69 engage opposing sides of a carrier 18 so that one post 69 can urge carrier 18 from carrier holding zone 56 and the other post 69 can urge carrier 18 from sampling position 26SP. Posts 69 are thereby enabled to engage and slide a sample tube carrier 18 between carrier holding zone 56 and sampling portion 26SP like seen in FIG. 10A in which sampling position 26SP is removed for purposes of illustration. In FIG. 9, sampling portion 26SP is illustrated as a element of analyzer 26 as is typical of many commercial analyzers. As discussed previously, however, an analyzer like analyzer 28 may be equipped with a robotic sampling probe and be operable to aspirate sample fluid directly from a sample tube 12 in sample tube carrier 18 without removing the sample tube carrier 18 from carousel 54 so that post pawl 69 and the source of linear motion 71 are unnecessary.

Figure 11:
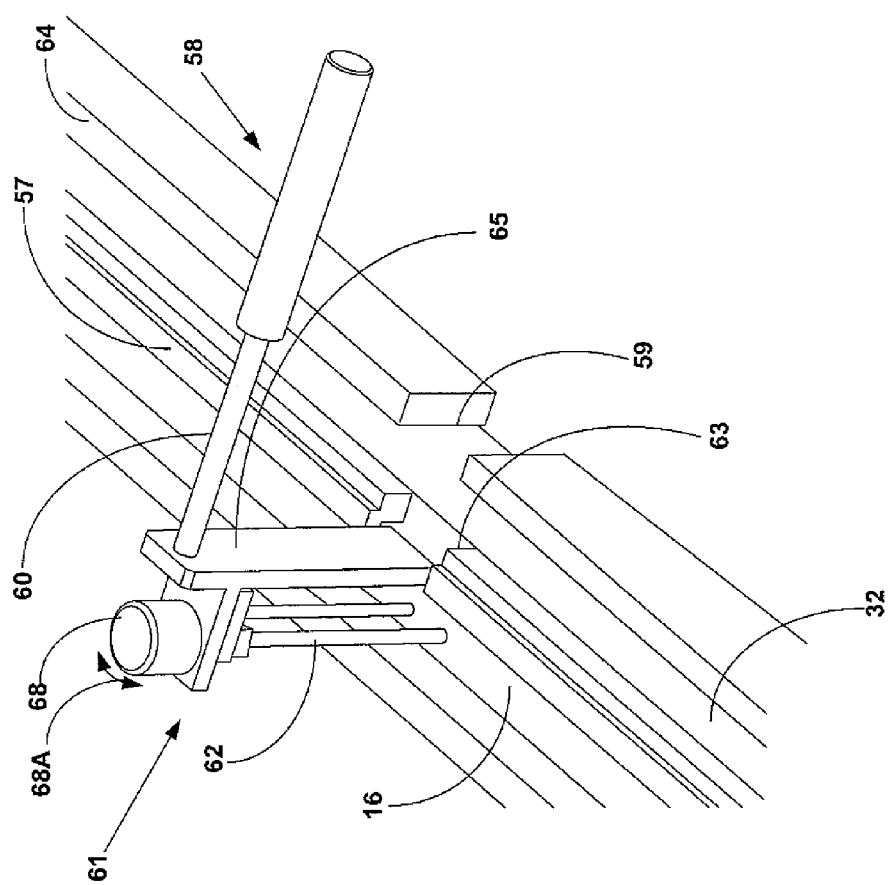
FIG. 11 is a simplified perspective view of a carrier shuttle advantageously employed in the present invention in a first position.
Figure 12B:
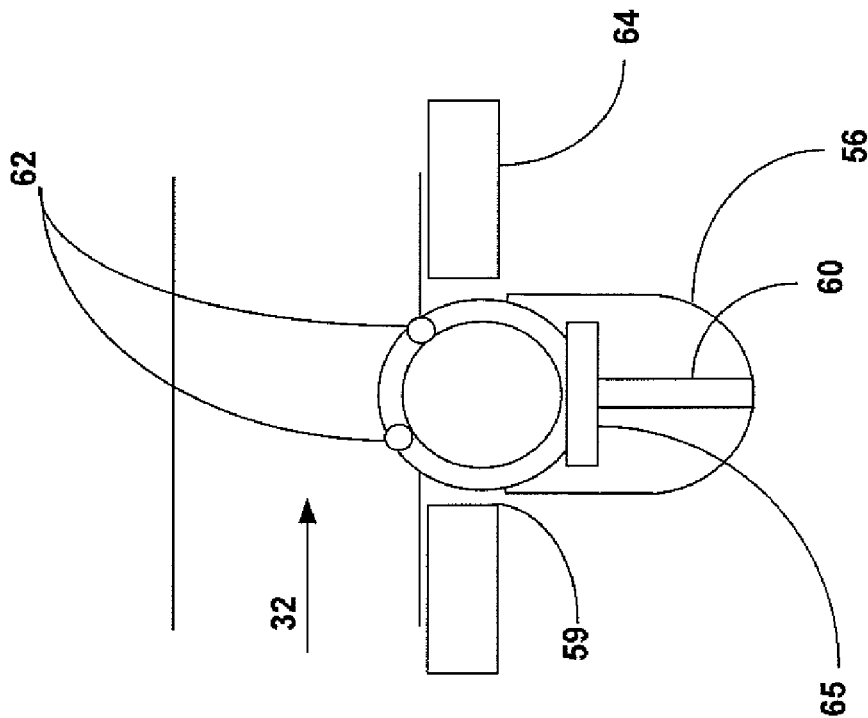
FIG. 12B is a simplified cut-away plan view of the carrier shuttle portion of FIG. 10 illustrating a carrier shuttle remove operating condition.
Figure 12A:
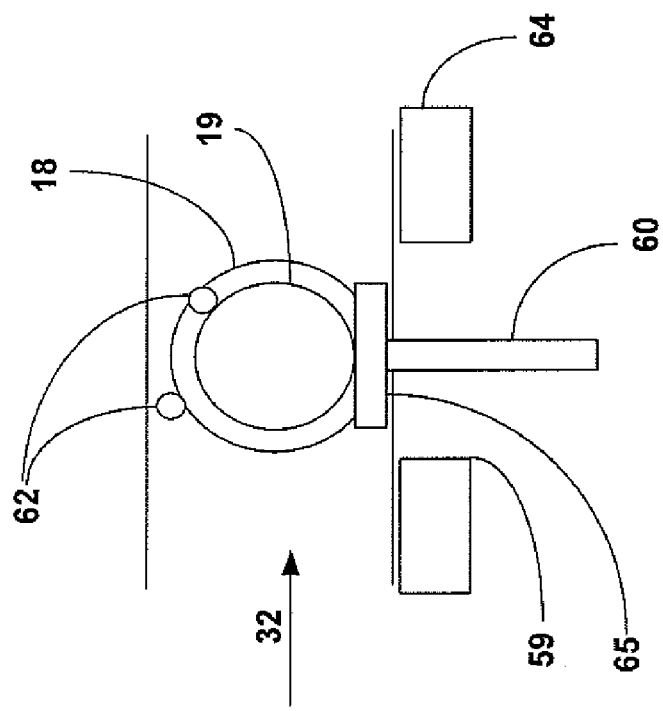
FIG. 12A is a simplified cut-away plan view of the carrier shuttle portion of FIG. 10 illustrating a carrier shuttle capture operating condition.
Figure 13B:
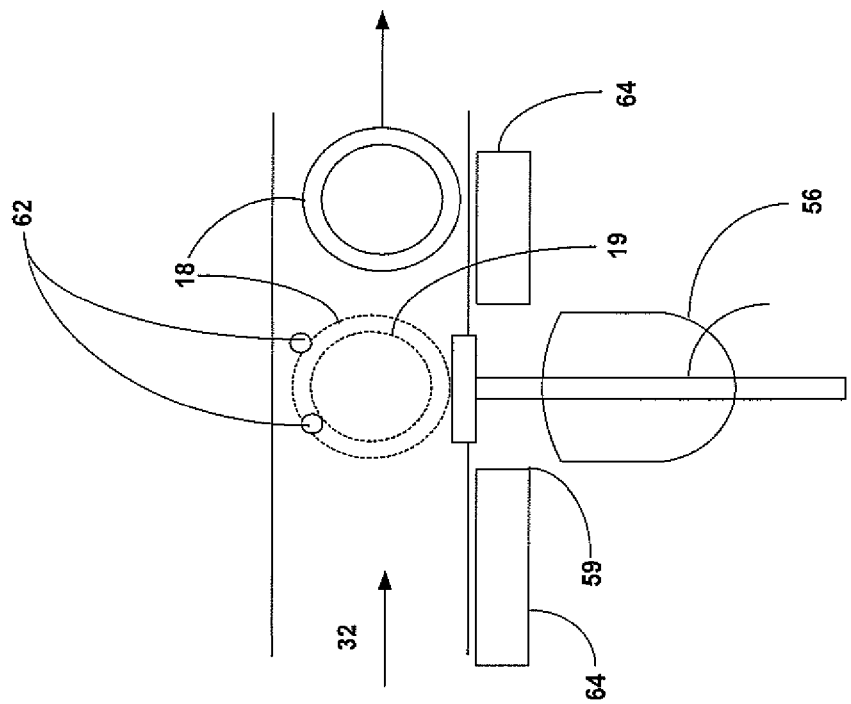
FIG. 13B is a simplified cut-away plan view of the carrier shuttle portion of FIG. 10 illustrating a release carrier shuttle operating condition.
Figure 13A:
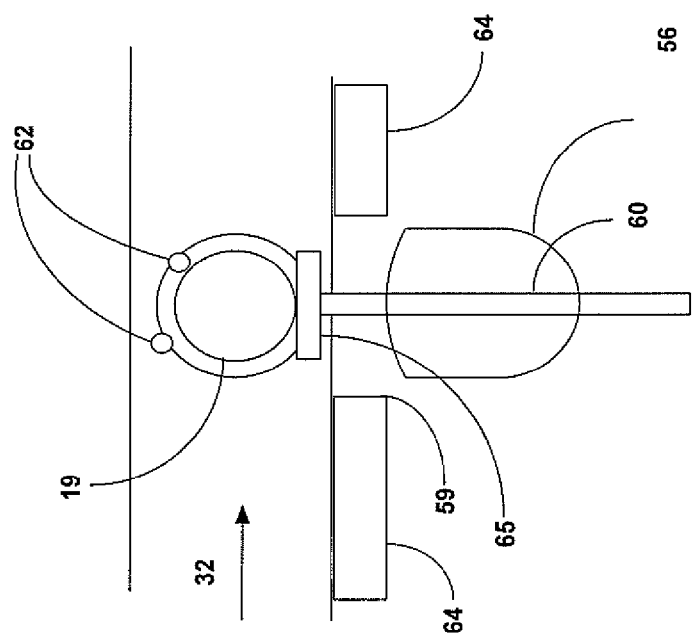
FIG. 13A is a simplified cut-away plan view of the carrier shuttle portion of FIG. 10 illustrating a replace carrier shuttle operating condition.

Escapement device 61 includes a pair of moveable rods 62 spaced apart and oriented appropriately to capture a single sample carrier 18 being transported on track 16 or 32. As is known to those skilled in the art, the design dimensions of the sample carrier 18 will affect design dimensions of the escapement device 61. FIG. 11 shows a simple but effective configuration in which a motor 68 is operable to bi-directionally rotate carrier shuttle rods 62 in a manner indicated by arrow 68A so as to engage and release sample tube carrier 18, for example on track 16. Although a number of different engaging actions may be employed, an exemplary action is illustrated in FIG. 12A wherein a sample tube carrier 18 is shown as moving from left to right on track 32 as indicated by an arrow. In FIG. 12A, motor 68 has rotated carrier shuttle rods 62 slightly clockwise from an orientation parallel to track 32 so that the raised central portion 19 of sample tube carrier 18 "slips past" the leftmost carrier shuttle rod 62 but the central portion 19 contacts the rightmost carrier shuttle rod 62 and travel of sample tube carrier 18 is stopped. In FIG. 12B, shuttle actuator 60 has been retracted so as to moveably slide sample carrier 18 from track 32, through opening 59 and onto a carrier holding zone 56 in rotatable carrier carousel 54. As discussed previously, after sample has been withdrawn from sample tube 12, carousel 54 may be rotated to re-align the sample tube carrier 18 with opening 59 and shuttle actuator 60 is extended to replace sample tube carrier 18 on track 32 as seen in FIG. 13A. Subsequently, at track 32 of FIG. 13B, motor 68 has rotated carrier shuttle rods 62 slightly counterclockwise so that the raised central portion 19 of sample tube carrier 18 is no longer constrained by the rightmost carrier shuttle rod 62 by contact with central portion 19 of carrier 18. Consequently, sample tube carrier 18 "slips past" the rightmost carrier shuttle rod 62 and moves rightward along track 32 as indicated by the arrow. The design of escapement device 61 will vary depending upon the nature and dimensions of tube carrier 18 and thus different mechanisms may be employed to capture, remove and replace and release a tube carrier along tracks 16 and 32.

Figure 14A:
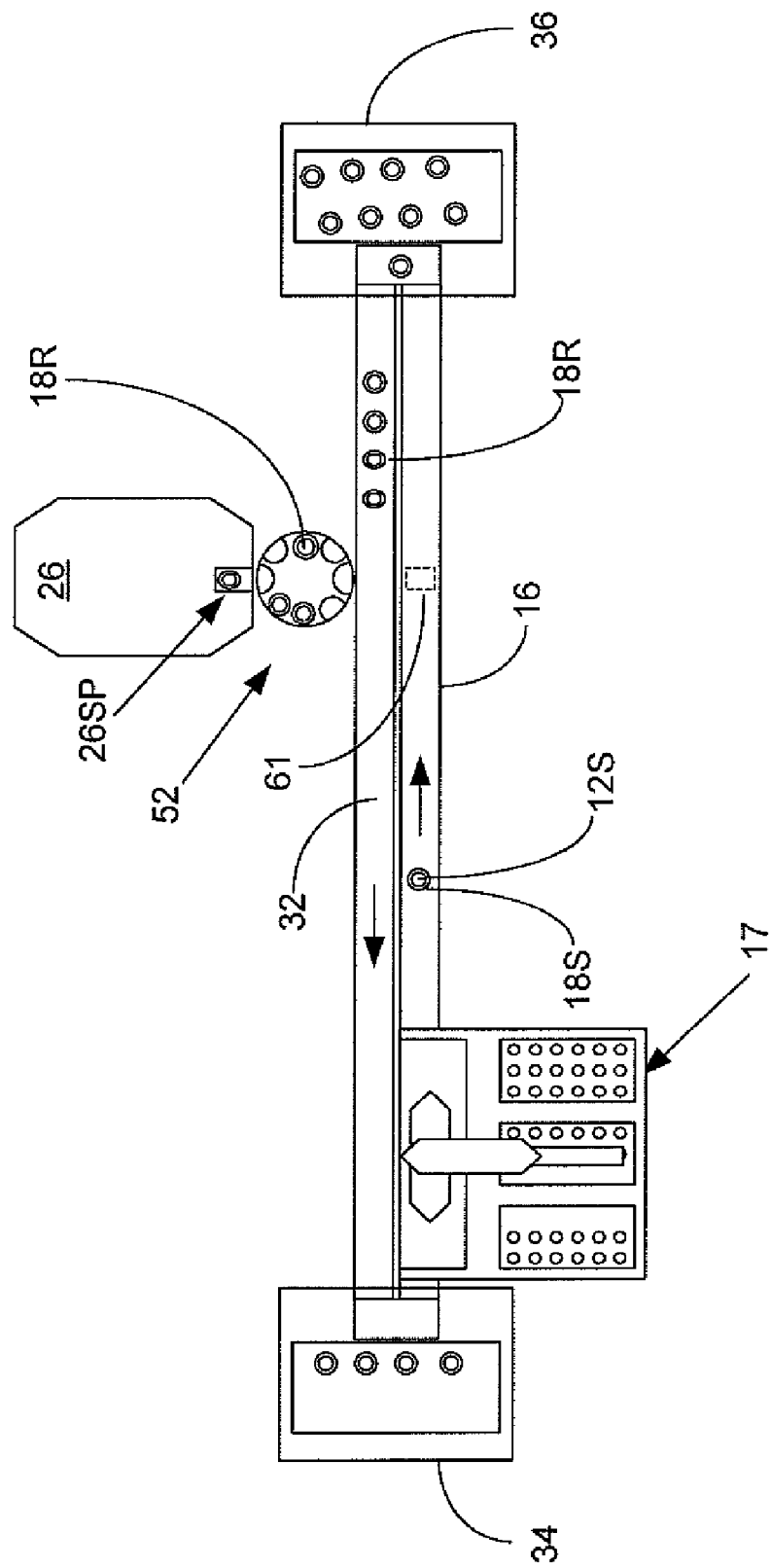
FIGS. 14A-B-C-D-E-F illustrate the sample handling buffer of the present invention presenting a "high priority" sample to an analyzer without delay from other sample tube carriers already scheduled to be processed by the same analyzer; and, FIGS. 15A and 15B illustrate the carrier shuttle portion of FIG. 10 removing and replacing a sample tube carrier onto the automated sample handling system of FIG. 1

FIG. 14A is a portion of FIG. 4 and illustrates sample handling buffer 52 of the present invention as enabling a special sample tube carrier 18S carrying a special sample tube 12S having a "high priority" sample requiring "immediate" analysis, to be placed on track 16 by sample tube loading/unloading robotic station 17 and then presented to analyzer 26 from conveyor track 16 in an, "out of turn" order without delay from other routine sample tube carriers 18R already scheduled to be processed by the same analyzer 26. In this example, four routine sample tube carriers 18R are "ahead" of sample tube carrier 18S on track 32 and in prior art systems, sample tube carrier 18S would move along track 16, be placed on track 32 by sample tube carrier transfer and buffering station 36 and approach analyzer 26 on track 32. In accord with the teachings of the present invention, carrier escapement device 61 is installed and is operable as seen in previous Figures, however, for purposes of clarity, escapement device 61 is seen in dotted lines and other portions of carrier shuttle 58 are not included.

Figure 14B:
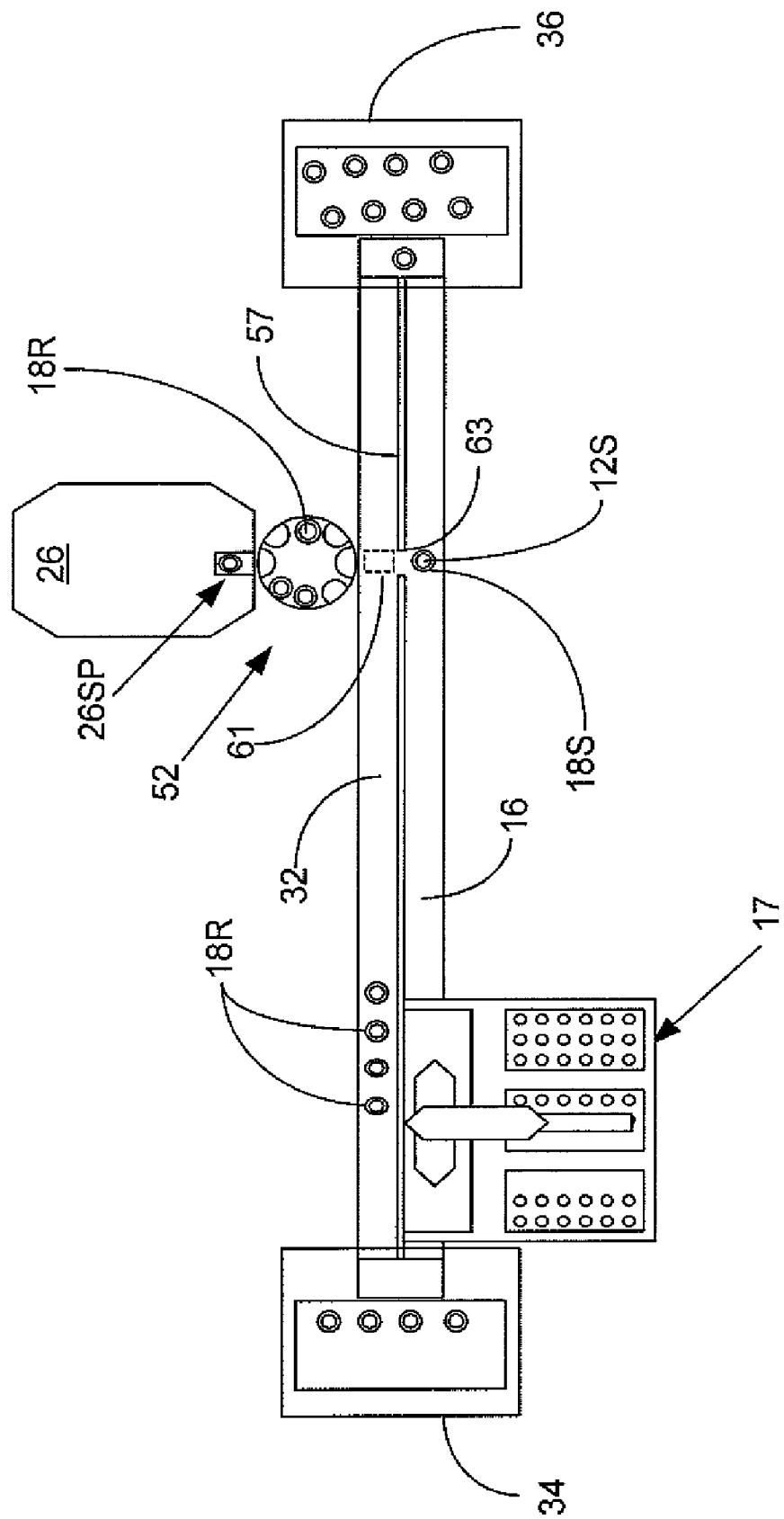
Figure 14C:
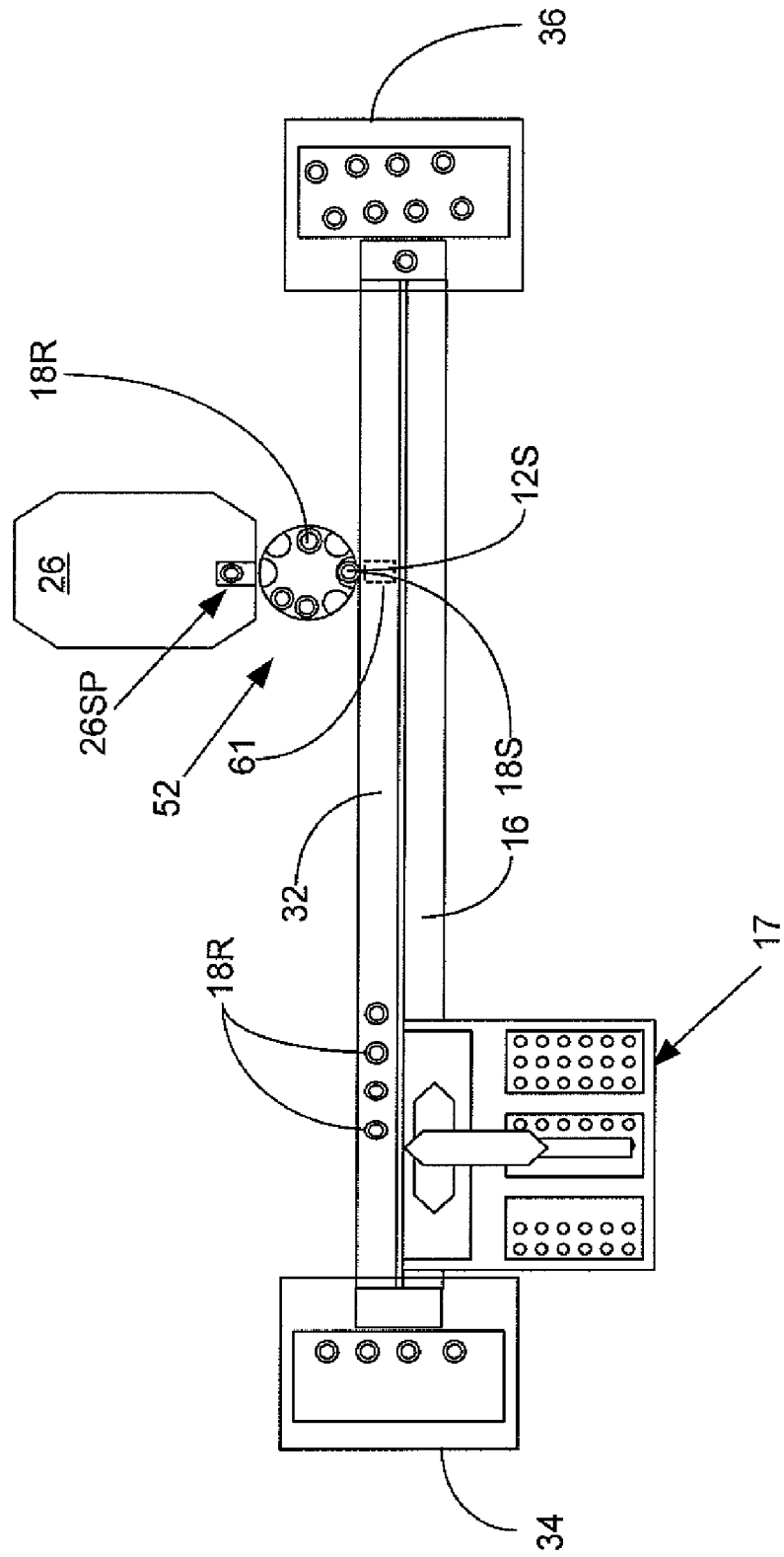
Figure 14D:
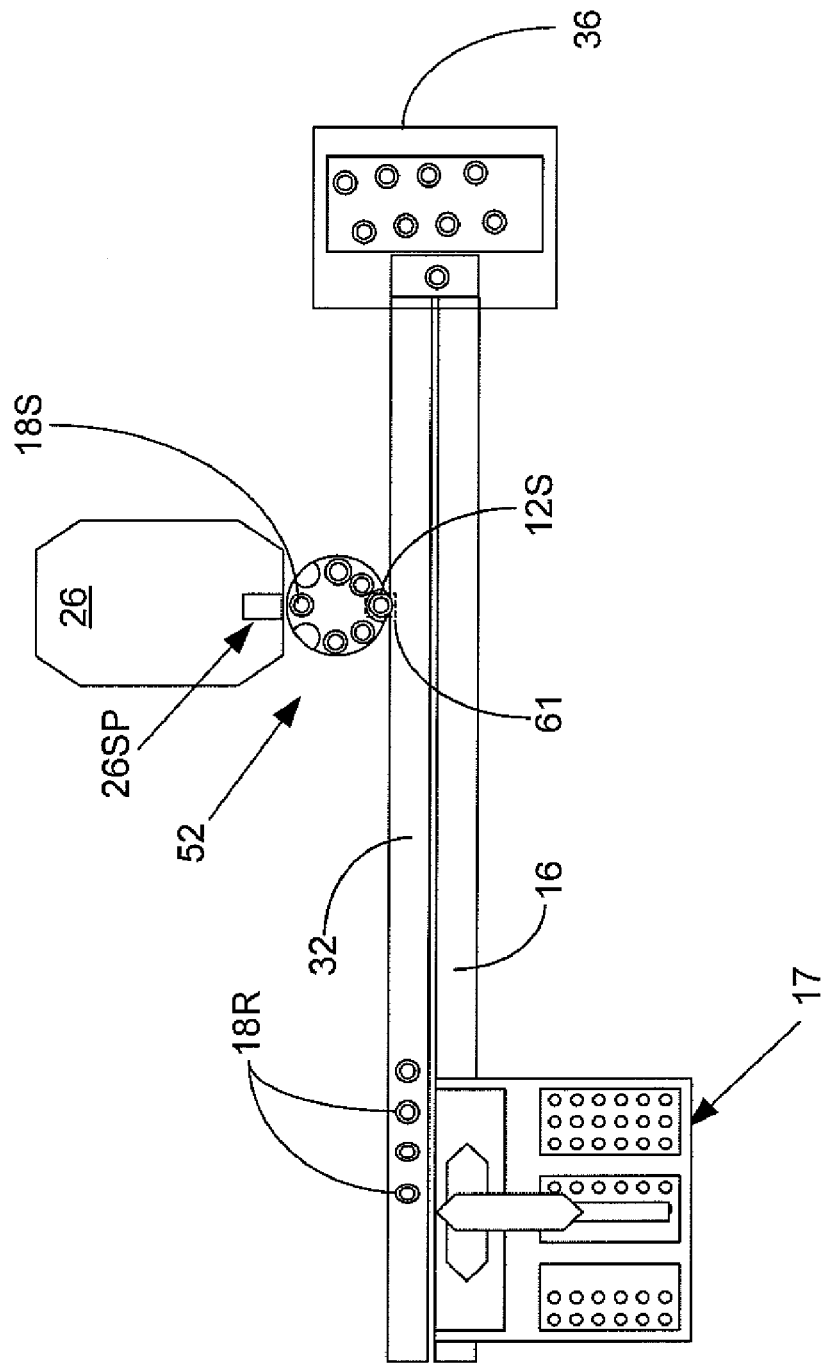
Figure 14E:
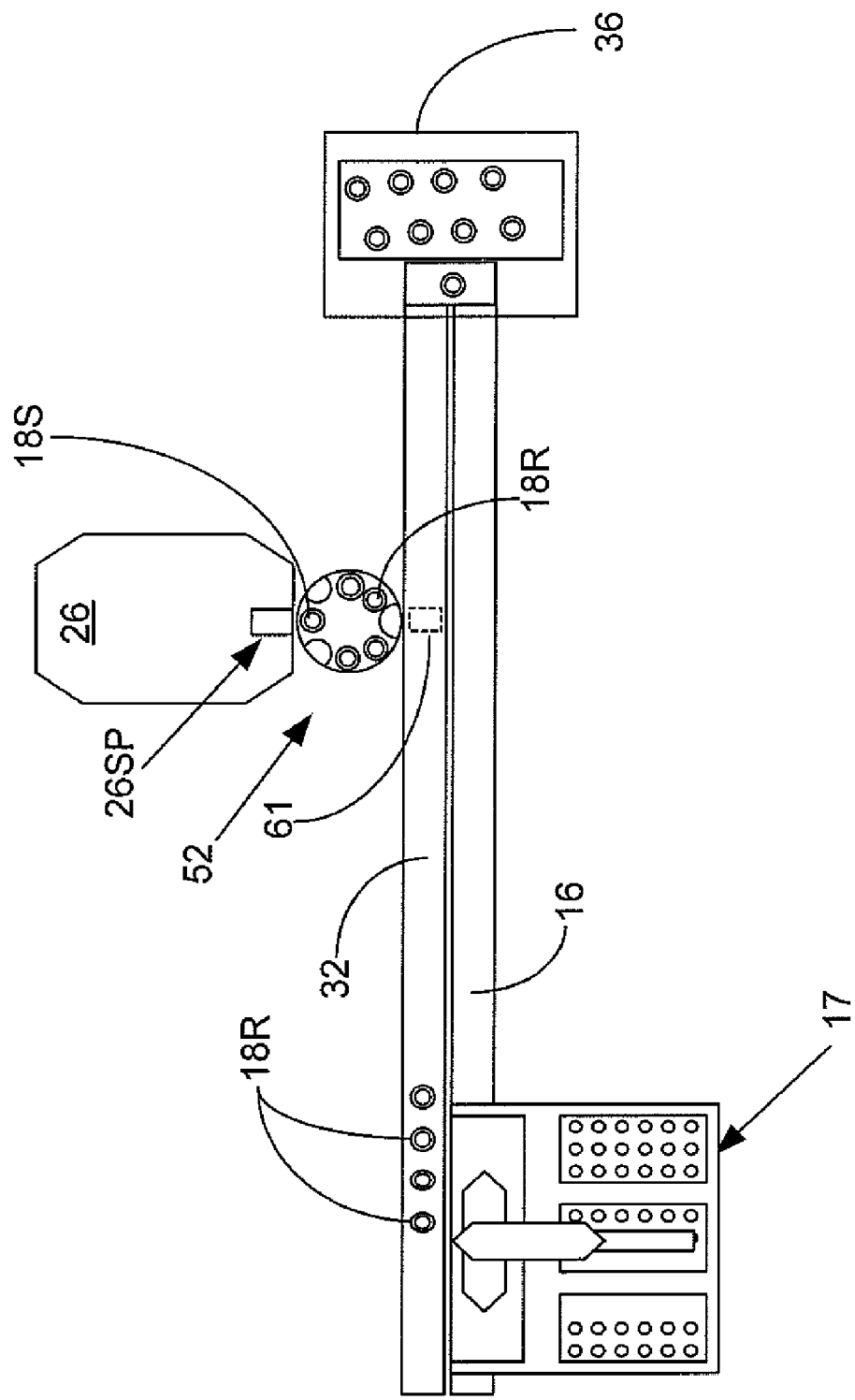
Figure 14F:
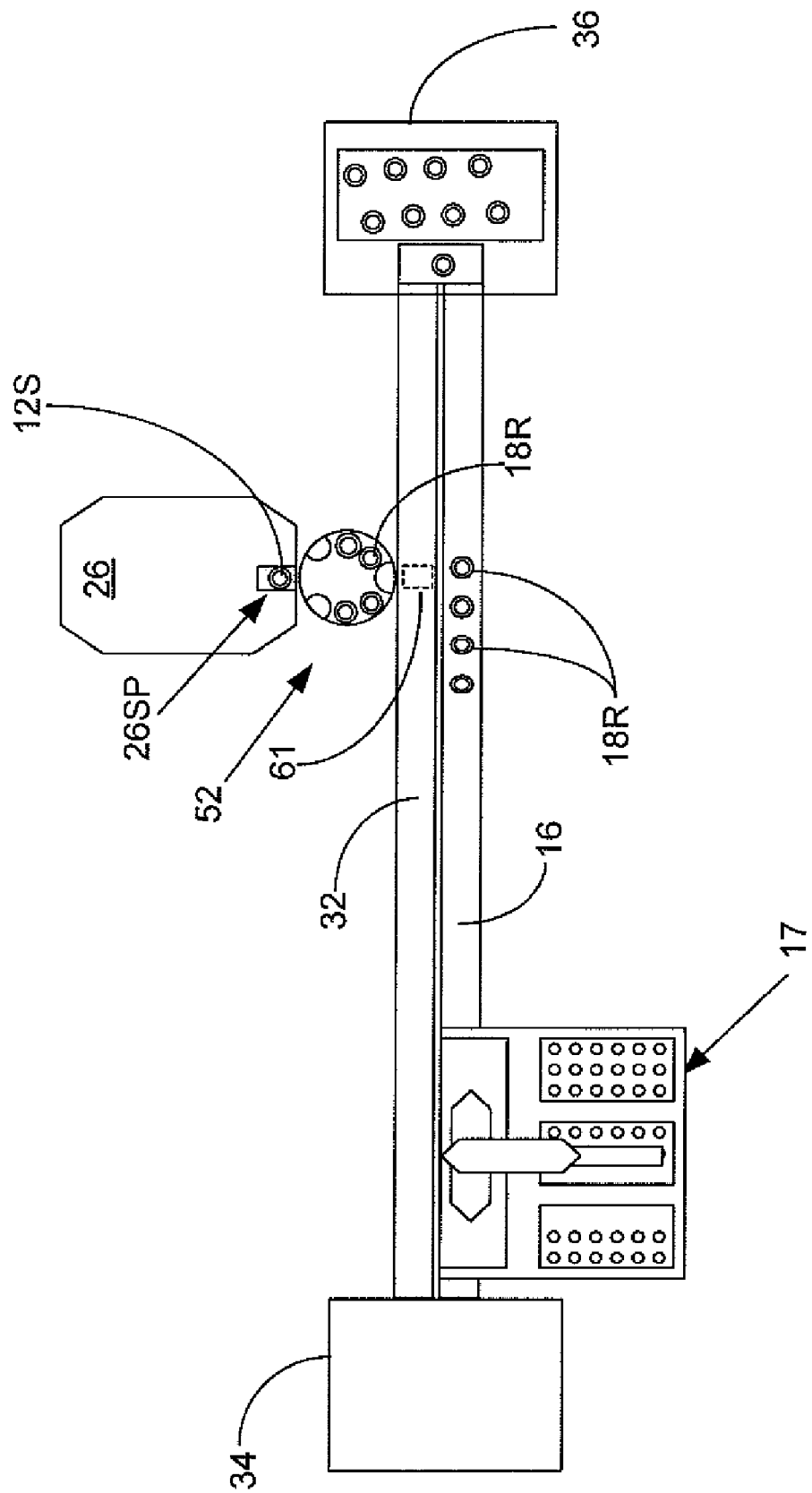

In an advantageous embodiment, the four routine sample tube carriers 18R "ahead" of special sample tube carrier 183 on track 32 are allowed to by pass analyzer 26 and be replaced on track 16 by buffering station 34 and will be processed after processing of special sample 123 is completed. Alternately, the four routine sample tube carriers 18R may be held upstream of analyzer 26 during the time special sample 123 is transferred to sampling portion 26SP. When special sample carrier 18S on track 16 is in position to be captured or engaged by carrier escapement device 61 at a location proximate opening 63 in rail 57 (as illustrated in FIG. 14B), then, as seen in FIGS. 14C and 14D, special sample tube carrier 188 is removed from track 16, transferred across track 32, through opening 59 in rail 64 and placed in a carrier holding zone 56 on carrier carousel 54. Carrier carousel 54 is then operated as explained in conjunction with FIGS. 5-8 so as to bring special sample carrier 18S directly into alignment with sampling portion 26SP of analyzer 26 (FIG. 14E) and then moved by carrier posts 69 into sampling position 26SP (FIG. 14F). Meanwhile, the original four routine sample tube carriers 18R previously "ahead" of special sample tube carrier 138 have been replaced on track 16 by buffering station 34 and may proceed to analyzer 26 for routine processing. This ability of the present invention, essentially comprising transferring a special sample tube carrier 18S directly from the sample tube loading/unloading robotic station 17 onto track 16 and from track 16 to carrier carousel 54 and therefrom into sampling position 26SP is a significant improvement over the prior art situation like illustrated in FIG. 1. After an appropriate amount of sample has been extracted from special sample tube 12S, FIGS. 15A and 15B illustrate special sample tube carrier 18S (dashed lines) removed from carrier holding zone 56 and replaced on track 32 and escapement device 62 slightly rotated counter-clockwise to as to release special sample tube carrier 18S (solid lines) onto track 32.

During the period of time that special sample carrier 18S remains in sampling position 26SP, the original four routine sample tube carriers 18R, or any other sample tube carriers 18 on tracks 16 or 32, can be captured by carrier escapement device 61 and placed in a carrier holding zone 56 on carrier carousel 54 using the procedure previously described in those instances when both carrier holding zones 56 on carousel 54 and transfer time are available. Alternatively, sample tube carriers 18 already in a carrier holding zone 56 can be replaced on track 16 or 32, by reversing the capturing procedure described. Clearly, because actuator 43 is adapted to align carrier holding zones 56 proximate sampling position 26SP in a sequence other than the sequence at which the sample tube carriers 18 are originally placed into carrier holding zones 56, then actuator 43 can cause carousel 54 to place any of the sample tube carriers 18 proximate the processing portion of analyzer 26 in any sequence, the same sequence or a sequence different from that at which the sample tube carriers 18 were transferred into carrier holding zones 56. Due to the "random handling" aspect of the present invention, sample tubes 12 come into the "random access" carousel 54 sequentially from the tracks 16 and 32. Once in carousel 54, tubes 12 can be presented to the sampling position 26SP in any order, not bound by the order tubes 12 arrived from tracks 16 and 32. While a sample tube 12 is being processed at the sampling position 26SP, carousel 54 is free to move as needed and sample tubes 12 can be moved into or out of the carousel 54. It is also possible that sample tubes 12 could be moved out of carousel 54 in a different order than they were received and possibly in a different order than tubes 12 were processed. It is also possible that a sample tube 12 could be returned to track 16 or 32 unprocessed as the result of a change in resources that makes it not possible to process the sample tube 12 at analyzer 26, or resources become available that make it more advantageous to process the sample at an alternate analyzer.

After an appropriate amount of sample has been extracted from special sample tube 12S, FIGS. 15A and 15B illustrate special sample tube carrier 18S (dashed lines) removed from carrier holding zone 56 and replaced on track 32 and escapement rods 62 slightly rotated counter-clockwise to as to release special sample tube carrier 18S (solid lines) onto track 32.

Figure 7:
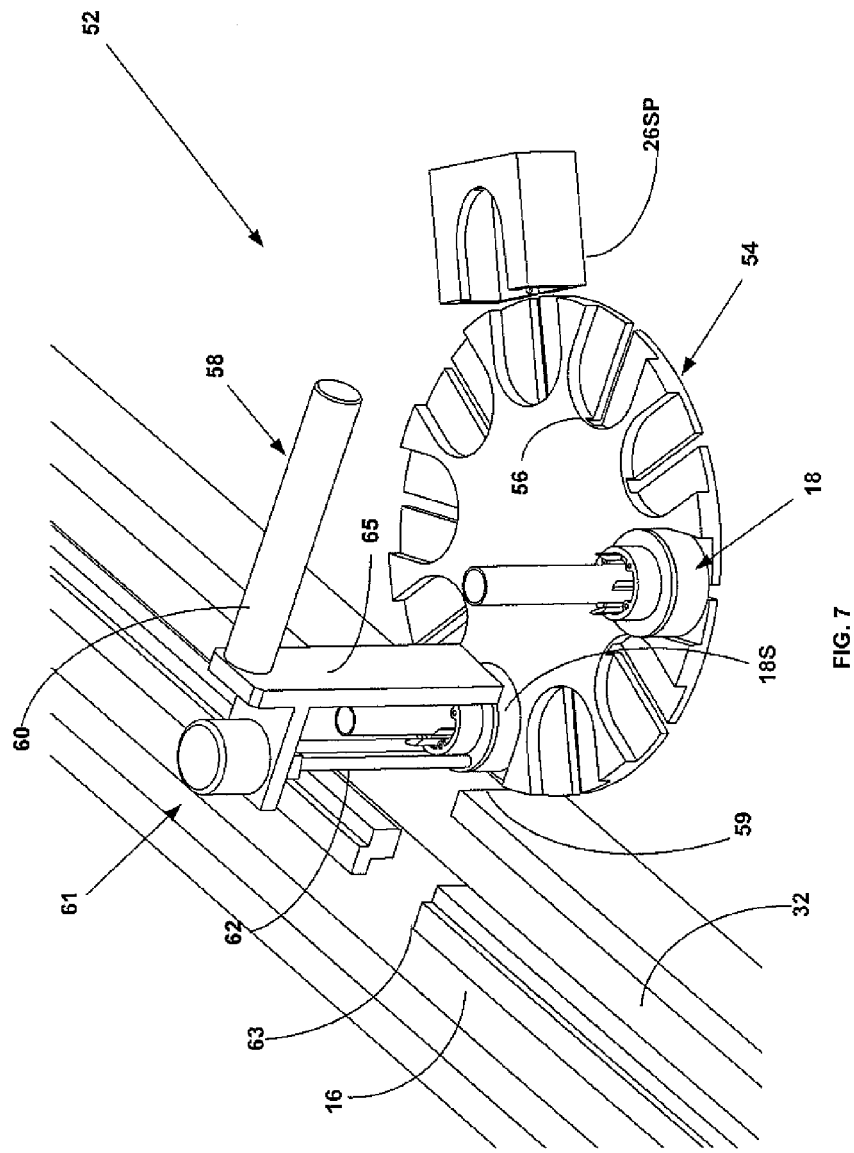
FIG. 7 is a simplified perspective view of the sample handling buffer of the present invention transferring the sample tube carrier of FIG. 6 onto a carrier carousel portion of the present invention.
Figure 8:
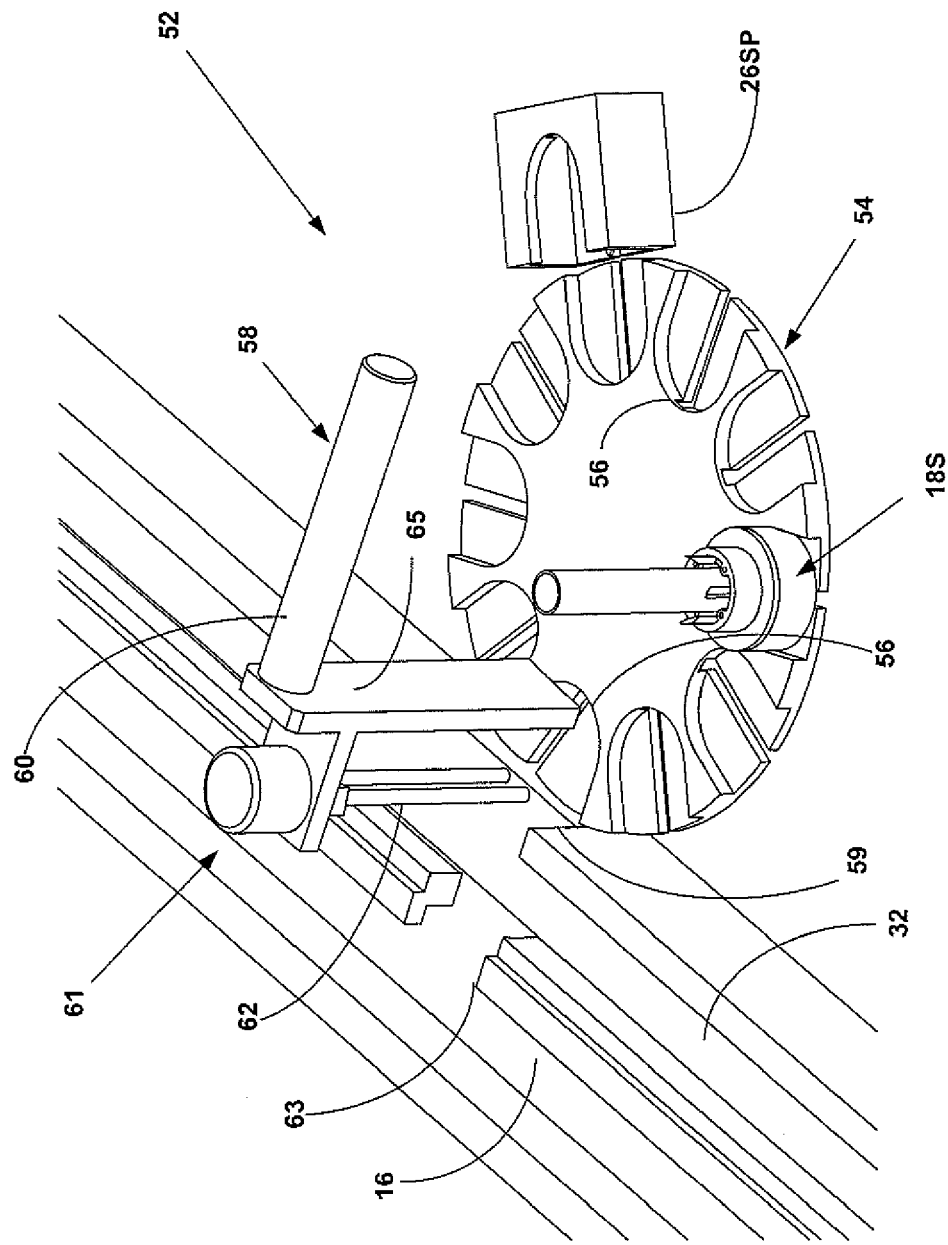
FIG. 8 is a simplified perspective view of the carrier carousel portion of the present invention transferring the sample tube carrier captured in FIG. 5 towards a sampling portion of an analyzer in FIG. 1.

In an alternate instance, sample handling buffer 52 could be operated as described in conjunction with FIGS. 6-8 so as to remove the four routine sample tube carriers 18R "ahead" of special sample tube carrier 18S from track 32 without presenting the sample tube carriers 18R to sampling position 26SP of analyzer 26. During this operation, any sample tube carriers 18 having sample tubes 12 from which samples have already been aspirated are removed from carousel 54 and/or sampling position 26SP and replaced on track 32. Sample handling buffer 52 is then operated so as to transfer the special sample tube carrier 18S from track 32 onto carousel 54 and to operate carousel 54 in order to bring special sample tube carrier 18S to sampling position 26SP of analyzer 26. In such instances, sample handling buffer 52 is operated such that at least one carrier holding zone 56 remains empty to accommodate special sample tube 12S. Sample handling buffer 52 thereby provides a method by which a special sample tube carrier 18S to be analyzed by clinical analyzer 26 on a high-priority or emergency basis can by-pass a number of "routine" sample tube carriers 18R waiting the queue or ahead of special sample tube carrier 18S and be presented for sampling at sampling position 26SP without delays experienced in prior art systems.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. For example, the sample carrier holder has been described as being a generally circular and rotatable carousel; however, in other embodiments, the sample carrier holder would be a continuous, elongate track having a number of carrier holding zones 56 formed therein, or a conventional, flat belt, and driven in alternate directions so as to remove and replace tube carriers 18 from tracks 16 and 32 in an expeditious manner. In addition, it is not necessary that a carrier holding zone 56 be formed in rotatable carrier carousel 54 as suitable alternatives, for example a ridge or pins in an upper flat surface can provide the equivalent function.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A sample handling buffer for removing a clinical sample carried in a sample carrier on a conveyor and presenting the sample to a sample processing station proximate said conveyor, the buffer comprising:
    a sample carrier holder proximate said conveyor and having a number of carrier zones formed therein, said zones sized to accept a sample carrier;
    a carrier shuttle having a carrier escapement device adapted to capture a sample carrier on the conveyor, the shuttle being operable to transfer the captured sample carrier into one of the carrier zones; and
    an actuator for causing said carousel to place the captured sample carrier proximate said processing station;
    wherein said conveyor comprises a pair of parallel tracks and said carrier shuttle is adapted to remove said sample carrier from either of said tracks.

2. The buffer of claim 1 wherein the carrier shuttle is further adapted to transfer a sample carrier from one of the carrier zones back onto the conveyor.

3. The buffer of claim 2 wherein the carrier shuttle is adapted to transfer a sample carrier from one of the carrier zones back onto the conveyor in the same sequence or in a different sequence than the sequence in which the sample carriers were transferred into the carrier zones.

4. The buffer of claim 1 wherein said actuator can cause said carousel to place any of the carrier holding zones proximate said processing station in any sequence, being the same sequence or other than the sequence at which the sample carriers were transferred into the carrier holding zones.

5. The buffer of claim 1 further comprising posts for transferring the captured sample carrier into and out of said processing station.

6. The buffer of claim 1 wherein said carrier shuttle is further adapted to replace and release said sample carrier onto either of said tracks.

7. The buffer of claim 1 wherein said carousel comprises a generally circular, rotatable plate and the carrier zones are formed in the outer circumference thereof.

8. The buffer of claim 1 wherein said sample processing station comprises an analyzer or a pre-analytical sample processing device.

9. A method for removing a clinical sample carried in a sample carrier on a conveyor and presenting the sample to a sample processing station proximate said conveyor, the method comprising:
    providing a sample handling buffer comprising a carousel proximate said conveyor and having a number of carrier zones formed therein, said zones sized to accept a sample carrier;
    operating a carrier shuttle having a carrier escapement device adapted to capture a sample carrier on the conveyor so as to transfer the captured sample carrier into one of the carrier zones; and
    placing the captured sample carrier proximate said processing station;
    wherein said conveyor comprises a pair of parallel tracks and said carrier shuttle is adapted to remove said sample carrier from either of said tracks.

10. The method of claim 9 wherein the carrier shuttle is further adapted to transfer a sample carrier from one of the carrier zones back onto the conveyor.

11. The method of claim 9 wherein said placing the captured sample carrier proximate said processing station comprises placing any of the carrier zones proximate said processing station in the same sequence or in a sequence other than the sequence in which the sample carriers were originally transferred into the carrier holding zones.

* * * * *

UNITED STATES PATENT AND TRADEMARK OFFICE
CERTIFICATE OF CORRECTION

PATENT NO.        : 7,681,466 B2                                    Page 1 of 1
APPLICATION NO.   : 11/742897
DATED             : March 23, 2010
INVENTOR(S)       : Miller et al.

It is certified that error appears in the above-identified patent and that said Letters Patent is hereby corrected as shown below:

1) On the title page Item (54); please delete "And" and insert --An--.
    2) In Column 8, line 11, please delete "pawls" and insert --posts--.
    3) In Column 8, line 28, please delete "pawl.".

Signed and Sealed this
Fourteenth Day of June, 2011

David J. Kappos
*Director of the United States Patent and Trademark Office*

UNITED STATES PATENT AND TRADEMARK OFFICE
CERTIFICATE OF CORRECTION

PATENT NO. : 7,681,466 B2
APPLICATION NO. : 11/742897
DATED : March 23, 2010
INVENTOR(S) : Miller et al.

Page 1 of 1

It is certified that error appears in the above-identified patent and that said Letters Patent is hereby corrected as shown below:

1) On the title page Item (54) and at Column 1, line 2, in the title, please delete "And" and insert --An--.
2) In Column 8, line 11, please delete "pawls" and insert --posts--.
3) In Column 8, line 28, please delete "pawl.".

This certificate supersedes the Certificate of Correction issued June 14, 2011.

Signed and Sealed this
Twelfth Day of July, 2011

David J. Kappos
*Director of the United States Patent and Trademark Office*